Nov. 11, 1958 E. B. LE GRICE Plant Pat. 1,769
NEW AND DISTINCT VARIETY OF ROSA HYBRID TEA PLANT
Filed Feb. 17, 1958
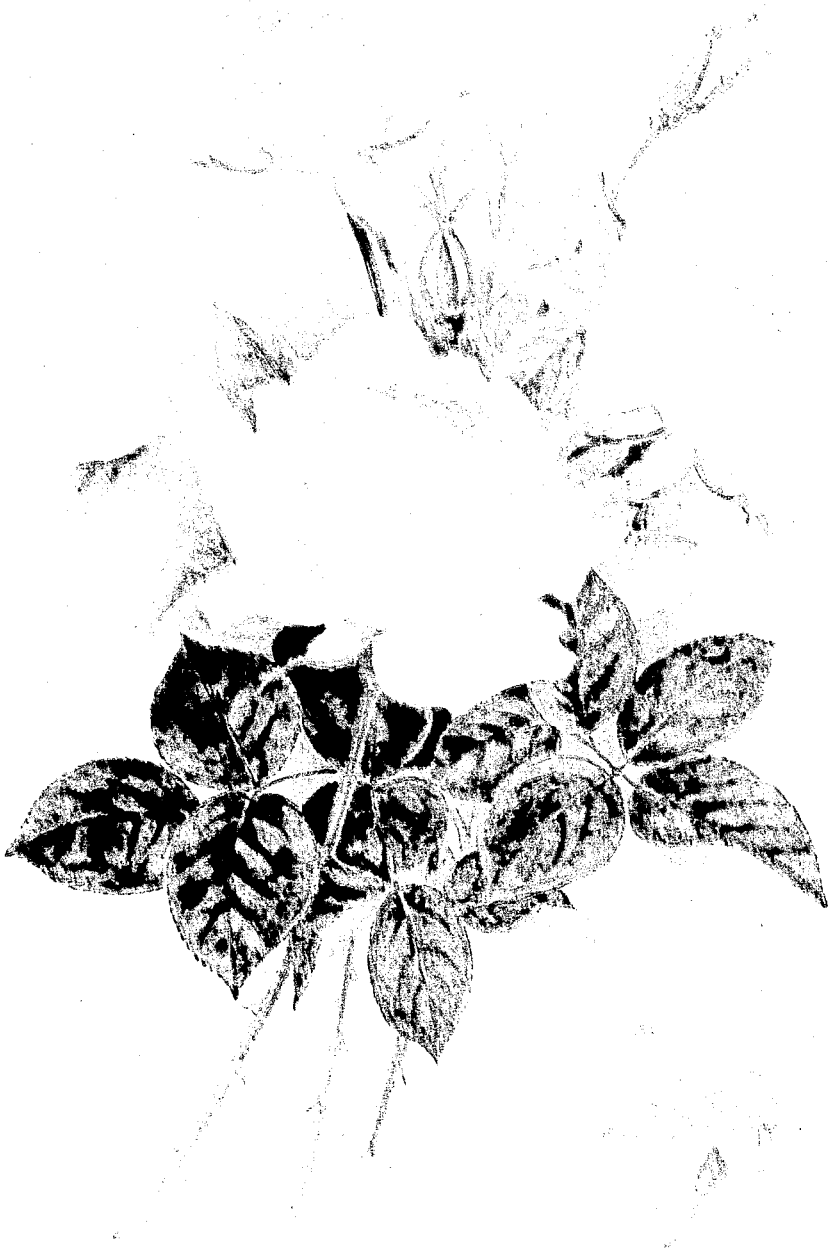
WITNESS
Addison E Avery
INVENTOR
Edward Burton Le Grice,
by:- John H Leonard,
his ATTY.

United States Patent Office

Plant Pat. 1,769
Patented Nov. 11, 1958

1,769

NEW AND DISTINCT VARIETY OF ROSA HYBRID TEA PLANT

Edward Burton Le Grice, North Walsham, England

Application February 17, 1958, Serial No. 715,842

1 Claim. (Cl. 47—61)

This invention relates to a new variety of hybrid tea rose plant.

The present rose plant was produced originally by the deliberate crossing of the rose known commercially as "Wellworth," as a seed parent, with the rose known commercially as "Ena Harkness," both unpatented.

"Ena Harkness" is a rose produced by crossing Southport, an unpatented variety, and Crimson Glory, Plant Patent No. 105. It is listed on page 31 of the 1958 edition of "Roses—a selected list of varieties," published by The National Rose Society of England. "Wellworth" is a rose produced by crossing Leontine Continot and Golden Dawn, both of which are unpatented varieties. It is listed in the above publication on page 85. The new variety was obtained by an intentional crossing of the parents. The plant is a definite hybrid having the growth characteristics of both parents.

The new variety was asexually reproduced by me, at my nurseries at North Walsham, England, by budding. The new variety has been tested in England, Belgium and South Africa.

The drawing shows in color a number of typical stalks with leaves, buds, blooms and thorns, together with a view of a single bloom with most of the petals removed to show the stamens and base of the inner petals.

The exposed plant is in the form of a hardy perennial bush of upright, symmetrical growth, flattened at the top. It grows generally to a height of about 2½ feet, and has a spread of about 2 feet for a one year old plant. Its growth is vigorous.

The exposed portion of the plant has a good resistance to low temperature when protected and unprotected. Its resistance both to drought and wet seasons is good.

For growth it prefers moderate sun and is generally indifferent as to exposure except for some preference for a southwest exposure. It thrives well in any good, well drained, mixed loam soil.

Hereafter, in referencing colors to charts, the colors are chosen from the British Colour Council Horticultural Colour Chart.

The main stalks of the plant are slightly branched. For this type of plant, they are relatively stiff and tough. They are of upright growth and are adequate to support the foliage and blooms well.

The new growth of the stalks is Lettuce Green, Chart 861/2 shaded increasingly on the underside to Pansy Purple, Chart 928/3.

The old growth is a Parsley Green, Chart 00962/3. On the old growth, the color is relatively uniform. On the new growth it is mottled.

The main stalks range from about 18 inches to 24 inches in length, and grow divergent upwardly. The upper flower stems are smooth, the lower slightly thorny.

The foliage in general is open and the leaf arrangement is whorled. The leaves are borne in medium quantity. The new leaves on the top surface are a Lettuce Green, Chart 861, veined and edged with Oxblood Red, Chart 00823. On the bottom surface they are Pea Green, Chart 61/2, shaded to the edges with Rose Bengal, Chart 25/1.

The old leaves, on the top surface, are Spinach Green, Chart 0960/1. On the bottom, they are Pod Green, Chart 061/1.

The leaves are medium in size and range, in length, 3 to 4½ inches and, in width, 2 to 3½ inches. They are of the usual shape, being pinnate with serrated margins, hastate bases, and acute apices. They are of average thickness. On the upper faces they are smooth and on the lower face dull and have smooth glands. Their persistency on the plant is good.

The petioles or leaf stems are an Oxblood Red, Chart 00823/3. They average in length about 1¼ inches and are quite strong. They are smooth textured.

The stipules are pronounced and in color are Pod Green, Chart 061.

The plant grows and blooms well in temperate regions. It prefers sun and a southwest exposure. It prefers wet seasons, and a well drained acid soil, preferably of a pH 6.5. It does best in a rich loam soil. A good soil and the preferred growing conditions improve the color of the blooms. Moist conditions increase the number of blooms and cool conditions appear to increase the size of the blooms. There is some fading of the blooms when growing in a strong sun.

The plant blooms from June through October, the blooming being recurrent for a period of about five months. Cutting of part of the flowers appears not to change the blooming characteristics or period.

The buds are of average to large size, slightly globular in shape, and smooth surfaces. They are borne upright and are terminal. The petal color, when the sepals first divide, is Crimson, Chart 22, and Straw Yellow, Chart 604.

When the petals begin to unfurl the color is Empire Yellow, Chart 603/1 on the reverse of the petals and Scarlet, Chart 19/2 on the inner face of the petals.

The sepals are of the usual shape and large.

The calyx is usual in shape and normal to large in size with a smooth surface texture.

The peduncles average from 8 to 12 inches in length, are strong, and have a smooth surface texture. The peduncles generally are Spinach Green, Chart 0960/3.

The pedicels average from 1½ to 2 inches in length. They have a smooth texture and are strong. Their color generally is Spinach Green, Chart 0960/3.

An increase in the temperature tends to hasten the blooming of the plant.

The blooms average from 4½ to 5 inches in diameter and the plant bears an average of 25 flowers. The blooms are borne singly. On the plant, and when cut, they last from 4 to 6 days. They normally have 35 petals.

The petalage is Empire Yellow, ranging from Chart 603 through Chart 603/1 and Chart 603/2, on the reverse. The inner face of the petals ranges from Scarlet, Chart 19/2, to Azalea Pink, Chart 618/3.

The general tonality of the plant from a distance, when it is in bloom, is Azalea Pink, Chart 618/3. With age, the tendency is to change from the Scarlet to the Azalea Pink on the inner face of the petals and to pale slightly on the reverse. The change during the blooming season is not pronounced.

The petals are smooth, thick and shiny on the inside. When in full bloom, the edges of the petals are rolled back. There are very few petaloids, five usually being the maximum. The persistence of the petals is good both for cut and uncut blooms. The flower has the usual arrangement of petals and general shape for roses of this type.

The fragrance of the blooms is a very strong, sharp damask. It is of good lasting quality, both in cut and uncut blooms.

The stamens are normal. In quantity they range from normal to many. In color, they are Buttercup Yellow, Chart 5/2. The filaments are of medium size and length. In color, they are Poppy Red, Chart 16. The pollen is Buttercup Yellow, Chart 5/2. The styles are, in size, about ⅛ inch and are Poppy Red, Chart 16. The stigmas, in size, are about 1/32 inch and are a Buttercup Yellow, Chart 5/2. Ovaries are medium in quantity.

The drawing further illustrates the characteristics of the variety and the following tabulation is a detailed description of the new variety:

*General*

Parentage:
- *Seed parent.*—"Wellworth," parentage unknown.
- *Pollen parent.*—"Ena Harkness," parentage unknown.

Classification: Bontainc—Rosa hybrid tea.

*Flower*

Blooming habit:
- *Location where observations were made.*—North Walsham, England. National Rose Trial Grounds, St. Albans, England. Also South Africa and Belgium.
- *Flowering.*—Recurrent for about five months from June until end of October.

Bud:
- *Size.*—Average to large.
- *Form.*—Slight globular.
- *Color.*—When sepals first divide petals are Crimson, Chart 22 to Straw Yellow, Chart 604. When petals begin to unfurl, they are Empire Yellow, Chart 603/1 on reverse and Scarlet, Chart 19/1 on the inner face. When half blown, they are Empire Yellow, Chart 603/1 on reverse and Scarlet, Chart 19/2, on inner face.
- *Sepals.*—Normal in shape and large.
- *Calyx.*—Normal to large in size with smooth texture.
- *Peduncle.*—Length 8 to 12 inches. Aspect—smooth. Color—Spinach Green, Chart 0960/3. Strong.
- *Opening.*—Normal, hastened by warm conditions.

Bloom:
- *Size.*—4½ to 5 inches in diameter.
- *Borne.*—Singly.
- *Stems.*—Length, 1½ to 2 inches; strong. Aspect—smooth. Color—Spinach Green, Chart 0960/3.
- *Form.*—When first opened—usual for type.
- *Permanence.*—On the plant or when cut—normal, 4 to 6 days.

Petalage:
- *Number of petals under normal conditions.*—35.
- *Color.*—Inside—Scarlet, Charts 19/1–2; reverse—Empire Yellow, Chart 603/1; base of petals—Empire Yellow, Chart 603.
- *Discoloration.*—Reverse pales slightly with age and inner face changes gradually from Scarlet to Azalea Pink, Chart 618/3.

Petals:
- *Texture.*—Thick.
- *Appearance.*—Shiny inside, smooth reverse.

- *Form.*—Usual, but edges roll back in full bloom.
- *Arrangement.*—Usual.
- *Petaloids in center.*—Few, up to 5.
- *Persistence.*—Good.
- *Fragrance.*—Very strong, sharp damask.
- *Lasting quality.*—On plant, good.

Genital organs:
- *Samens.*—Normal. Color — Buttercup Yellow, Chart 5/2. Arrangement—normal.
- *Filaments.*—Medium length. Color—Poppy Red, Chart 16.
- *Pollen.*—Buttercup Yellow, Chart 5/2.
- *Styles.*—⅛ of an inch, colored Poppy Red, Chart 16.
- *Stigmas.*—About 1/32 inch, colored Buttercup Yellow, Chart 5/2.
- *Ovaries.*—Medium quantity.

*Plant*

Form: A hardy perennial bush, upright growth with symmetrical contour and flat top.

Growth: Vigorous, about 2½ feet high and with a spread of 2 feet for a one year old plant.

Foliage: Open and whorled.
- *Size.*—Medium length, ranging in length 3 to 4½ inches and in width 2 to 3½ inches.
- *Quantity.*—Medium.
- *Color.*—New leaves, on top, Lettuce Green, Chart 861, veined and edged with Oxblood Red, Chart 00823/3. Bottom, Pea Green, Chart 61/2 shaded to edges with Rose Bengal, Chart 25/1. Old leaves, on top, Spinach Green, Chart 0960/1 and Pod Green, Chart 061/1 on bottom.
- *Shape.*—Usual.
- *Texture.*—Upper face, smooth; lower face, dull.
- *Edge.*—Serrated.

Petiole: Length, about 1¼ inches, with smooth texture. Color—Oxblood Red, Chart 00823/3.

Stipules: Pod Green, Chart 061.

Wood:
- *Newest wood.*—Color, Lettuce Green, Chart 861/2, on exposed side with Pansy Purple, Chart 928/3.
- *Bark.*—Smooth.
- *Old wood.*—Color, Parsley Green, Chart 00962/3.
- *Bark.*—Smooth.

Thorns:
- *Quantity.*—Practically none on upper flower stems, slightly thorny on lower.
- *Form.*—Short.
- *Color.*—Brown.
- *Position.*—Evenly distributed on lower flower stalks, few or none on upper.

The most distinctive features and characteristics of the new hybrid tea rose plant are its vigorous growth, the pleasing color and sweet perfume of the flowers, the many flowers borne, all of which produce a plant useful for exhibition and very fine in bedding.

Having shown and described my new variety of hybrid tea rose plant, and its manner of asexual reproduction, I claim:

The new and distinct variety of hybrid tea rose plant herein shown and described.

No references cited.